United States Patent
Damour et al.

(10) Patent No.: US 10,451,209 B2
(45) Date of Patent: Oct. 22, 2019

(54) SEGMENT OF PIPE-IN-PIPE PIPELINE AND THE USE OF AN ACOUSTIC TRANSDUCER MEASUREMENT SYSTEM FOR THE REDUCED PRESSURE ANNULUS

(71) Applicant: ITP SA, Louveciennes (FR)

(72) Inventors: Jean-Aurélien Damour, Louveciennes (FR); Christian Geertsen, Versailles (FR); Pierre Ollier, Boulogne Billancourt (FR)

(73) Assignee: ITP SA, Louveciennes (FR)

( * ) Notice: Subject to any disclaimer, the term of this patent is extended or adjusted under 35 U.S.C. 154(b) by 0 days.

(21) Appl. No.: 15/920,021

(22) Filed: Mar. 13, 2018

(65) Prior Publication Data

US 2018/0259111 A1    Sep. 13, 2018

(30) Foreign Application Priority Data

Mar. 13, 2017  (FR) ..................... 17 70244

(51) Int. Cl.
| | |
|---|---|
| *F16L 55/26* | (2006.01) |
| *E21B 17/00* | (2006.01) |
| *E21B 36/00* | (2006.01) |
| *E21B 47/06* | (2012.01) |
| *G01K 1/02* | (2006.01) |

(Continued)

(52) U.S. Cl.
CPC ........... *F16L 55/265* (2013.01); *E21B 17/00* (2013.01); *E21B 36/003* (2013.01); *E21B 47/06* (2013.01); *E21B 47/065* (2013.01); *F16L 9/18* (2013.01); *F16L 59/065* (2013.01); *F17D 5/06* (2013.01); *G01K 1/024* (2013.01); *G01L 11/04* (2013.01); *G01L 19/086* (2013.01);

(Continued)

(58) Field of Classification Search
CPC ......... F16L 55/265; F16L 9/18; F16L 59/065; E21B 17/00; E21B 36/003; E21B 47/06; E21B 47/065; G01K 1/024; G01L 19/086
See application file for complete search history.

(56) References Cited

U.S. PATENT DOCUMENTS

| | | |
|---|---|---|
| 4,111,040 A | 9/1978 | Gratacos et al. |
| 5,594,705 A | 1/1997 | Connor et al. |

(Continued)

FOREIGN PATENT DOCUMENTS

| | | | |
|---|---|---|---|
| EP | 0148591 A1 * | 7/1985 | .............. G01L 11/04 |
| WO | 2015/016927 A1 | 2/2015 | |

OTHER PUBLICATIONS

Oct. 30, 2017 Preliminary Search Report issued in French Patent Application No. 1770244.

*Primary Examiner* — Amine Benlagsir
(74) *Attorney, Agent, or Firm* — Oliff PLC

(57) ABSTRACT

The invention relates to a segment of pipe-in-pipe pipeline comprising an annulus under reduced pressure sealed and delimited by a metallic internal pipe inserted into a metallic external pipe and provided with a measurement system to determine in a non-intrusive manner the state of the annulus, the measurement system being composed of a first internal emitter/receiver assembly placed inside the annulus and cooperating with means to measure a first physical quantity such as pressure, hygrometry or temperature inside the reduced pressure annulus and a second external emitter/receiver assembly arranged to the exterior of the segment and facing said first assembly.

7 Claims, 4 Drawing Sheets

(51) Int. Cl.

| | |
|---|---|
| *G01L 19/08* | (2006.01) |
| *G01N 19/10* | (2006.01) |
| *F16L 59/065* | (2006.01) |
| *F16L 9/18* | (2006.01) |
| *G01L 11/04* | (2006.01) |
| *F17D 5/06* | (2006.01) |
| *G01M 3/24* | (2006.01) |
| *F16L 59/147* | (2006.01) |

(52) U.S. Cl.
CPC ............ *G01M 3/243* (2013.01); *G01N 19/10* (2013.01); *F16L 59/147* (2013.01); *F16L 2201/30* (2013.01)

(56) References Cited

U.S. PATENT DOCUMENTS

| | | | |
|---|---|---|---|
| 2010/0229662 A1* | 9/2010 | Brower | F16L 59/141 73/865.8 |
| 2014/0145857 A1* | 5/2014 | Comparetto | E21B 47/12 340/854.6 |
| 2016/0138385 A1* | 5/2016 | Cortez | E21B 47/082 166/250.01 |
| 2017/0016319 A1* | 1/2017 | Kyle | E21B 47/16 |
| 2017/0081956 A1* | 3/2017 | Ganguly | E21B 47/122 |

\* cited by examiner

SEGMENT OF PIPE-IN-PIPE PIPELINE AND THE USE OF AN ACOUSTIC TRANSDUCER MEASUREMENT SYSTEM FOR THE REDUCED PRESSURE ANNULUS

BACKGROUND OF THE INVENTION

1. Field of Invention

The technical scope of the present invention is that of metallic pipe-in-pipe pipelines used for the transportation of hydrocarbons.

2. Description of the Related Art

In the on-shore or off-shore exploitation of hydrocarbons, a thermally insulated pipe-in-pipe pipeline may be used. Such exploitation relates, for example, to heavy oils containing hydrates or paraffins likely to solidify, thereby blocking the pipeline leading to its being disabled.

The pipe-in-pipe pipelines in question are typically thermally insulated pipes with screw connections for oil wells or steam injection wells and heated hydrocarbon pipes assembled by welding for the transportation of oil or gas for sub-sea or land operations.

A segment of thermally insulated pipe-in-pipe integrates, for example, a silica-based open-pore thermally insulating material, arranged in the annulus delimited by a metallic inner pipe and a metallic outer pipe. This space is closed and sealed and put under reduced pressure so as to improve the thermal performance of the insulating material.

Another insulating technology consists in using a multi-layer insulator associated with a highly reduced pressure, known as high vacuum or secondary vacuum.

During the manufacture of these pipe-in-pipe segments of 6 to 60 m, the annulus is put under reduced pressure just before being closed and sealed. Reduced pressure means a pressure of less than $10^5$ Pa. At the end of these operations, it is no longer possible for the pressure in the annulus to be immediately and directly measured. It is only possible for it to be estimated by carrying out a thermal test. One pipeline may comprise several hundred or even several thousand pipe segments.

To date, there are no means enabling an economical, direct and immediate measurement, for example using a sensor, of the pressure in the multiple annuluses put under reduced pressure.

Document WO 2015/0169927 is known, which proposes the measurement of a factor of the pressure, temperature, pH type in the riser of an oil well. Two acoustic coupling elements are provided arranged facing each other on opposite sides of the riser. These coupling elements are piezoelectric elements to emit and receive acoustic signals. The coupling element placed on the inner side is powered from the exterior. The coupling element on the exterior side is linked to a fluid analysis assembly communicating with the interior of the riser via a drill hole. There is thus no detection assembly arranged facing it and the analysis requires a hole to be drilled in the riser.

U.S. Pat. No. 5,594,705 is also known, which discloses a device to measure the pressure inside the hull of a ship. This device comprises a primary device arranged in the environment surrounding the ship and a secondary element positioned inside the hull.

All the prior art shows that it has never been possible or envisaged to determine the state of an annulus of a pipe-in-pipe pipeline, when being sealed during its manufacture, so as to measure physical quantities such as pressure, temperature or hygrometry. This concern, however legitimate, has never been solved in an economical and reliable manner.

This is why the applicant thought of integrating means into the annulus, from the manufacturing phase of the pipe-in-pipe, so as to obtain these measurements without inflicting damage on the pipeline.

SUMMARY OF THE INVENTION

The aim of the present invention is thus to supply a segment of pipe-in-pipe pipeline that enables the state of a reduced pressure annulus to be determined by the measurement of different quantities without any modification of the structure of the external pipe as well as the use of a transducer system to this end.

The invention thus relates to a segment of pipe-in-pipe pipeline comprising a reduced pressure annulus sealed and delimited by a metallic internal pipe inserted into a metallic external pipe and provided with a measurement system to determine in a non-intrusive manner the state of the annulus, the measurement system being composed of a first internal emitter/receiver assembly cooperating with means to measure a first physical quantity such as pressure, hygrometry or temperature inside the reduced pressure annulus and a second external emitter/receiver assembly arranged to the exterior of the segment and facing said first assembly.

According to a first characteristic of the invention, the segment incorporates means arranged on the outer wall of the external pipe to locate the position of said first assembly based on a predetermined point of the latter.

According to another characteristic of the invention, the first internal emitter/receiver assembly is a first acoustic transducer fixed to the inner wall of the external pipe and the second external emitter/received assembly is a second acoustic transducer arranged on the outer wall of the external pipe.

According to another characteristic of the invention, the first internal emitter/receiver assembly is a first acoustic transducer fixed to the outer wall of the internal pipe and the second external emitter/receiver assembly is a second acoustic transducer arranged against the inner wall of the internal pipe.

Advantageously, the first and second transducers are formed to fit the curvature of the respectively internal and outer walls of the external pipe.

Advantageously again, the first transducer comprises a physical quantity measurement sensor associated with acquisition electronics and the second transducer comprises an external communication module associated with a data receiver or transmitter interface.

According to yet another characteristic of the invention, the first and second emitter/receiver assemblies are formed by electromagnetic induction loops.

According to yet another characteristic of the invention, the first emitter/receiver assembly is powered by batteries.

The invention also relates to the use of an acoustic transducer system to determine, in a non-intrusive manner, the state of a sealed reduced pressure annulus of a segment of pipe-in-pipe pipeline such as defined previously.

Advantageously, the use of the transducer system to study the annulus of a segment of pipe-in-pipe pipeline is performed in an environment that is at high temperature, cryogenic or subjected to an ageing cycle.

Advantageously, the use of a transducer system is applied to the study of an annulus of a pipe-in-pipe pipeline of great length or where the pressure in the annulus is to be monitored at several points along the pipeline.

In the application according to the invention, the transducers are shaped to fit the curvature of the external pipe wall.

A first advantage of the present invention lies in the fact that for the first time, it is possible to access the reduced pressure annulus of a pipe-in-pipe pipeline so as to obtain data on the pressure, temperature, hygrometry or other physical quantities.

Another advantage of the invention lies in the fact that there is no alteration of the external pipe to determine the value of the physical quantities to be measured.

Yet another advantage of the invention lies in the fact that the measurements may be made throughout the lifetime of the pipe-in-pipe pipeline.

Yet another advantage of the present invention lies in the potential of following-up on quality for a factory production.

Yet another advantage of the invention lies in the possibility of performing qualification tests of a long duration for a pipe-in-pipe pipeline. In particular, measurement of the reduced pressure may be performed over durations of one year or even of several years to ensure the lifetime of this reduced pressure present in the annulus of the pipeline.

BRIEF DESCRIPTION OF THE DRAWINGS

Other characteristics, advantages and particulars of the invention will become more apparent from the additional descriptions hereafter of the different embodiments, given by way of example and in reference to the drawings, in which.

DETAILED DESCRIPTION OF PREFERRED EMBODIMENTS

Hereafter in this technical description, the terms "a pipe-in-pipe pipeline segment" or a "pipe-in-pipe pipeline" will be used indifferently.

The invention will now be described in greater detail. As explained previously, when the annulus of a pipe-in-pipe pipeline segment is sealed it is no longer possible to access it. The pipeline in question is formed of a certain number of elementary segments, for example of a length of 12 or 24 m, connected together to form pipelines of 1 to 10 km.

Classically, each pipeline segment comprises an inner pipe, inside which the fluid in question flows, and an outer pipe that delimit between them an annulus. This annulus is filled namely with a silica-based open-pore thermally insulating material or an anti-radiation multilayer assembly. Each annulus of each segment is thus closed and sealed at the two ends of the two pipes and thus constitutes a confined space. This confined space is of small dimension and may be of between 4 and 10 mm for pipes of a diameter of less than 150 mm, between 8 and 25 mm for pipes of a diameter of less than 400 mm and less than 60 mm for pipes of larger diameters.

To improve the thermal performances of the thermal insulation and thus of the pipe-in-pipe pipeline, the pressure inside this confined space is reduced. When these segments are being manufactured, the reduction in pressure is made just before the annulus is sealed closed. Reduced pressure means pressure of less than atmospheric pressure, for example 100 mbar.

At this point, to go from an estimation of the pressure in the annulus to an actual and precise measurement of the pressure, the following process is employed.

Figure 1:
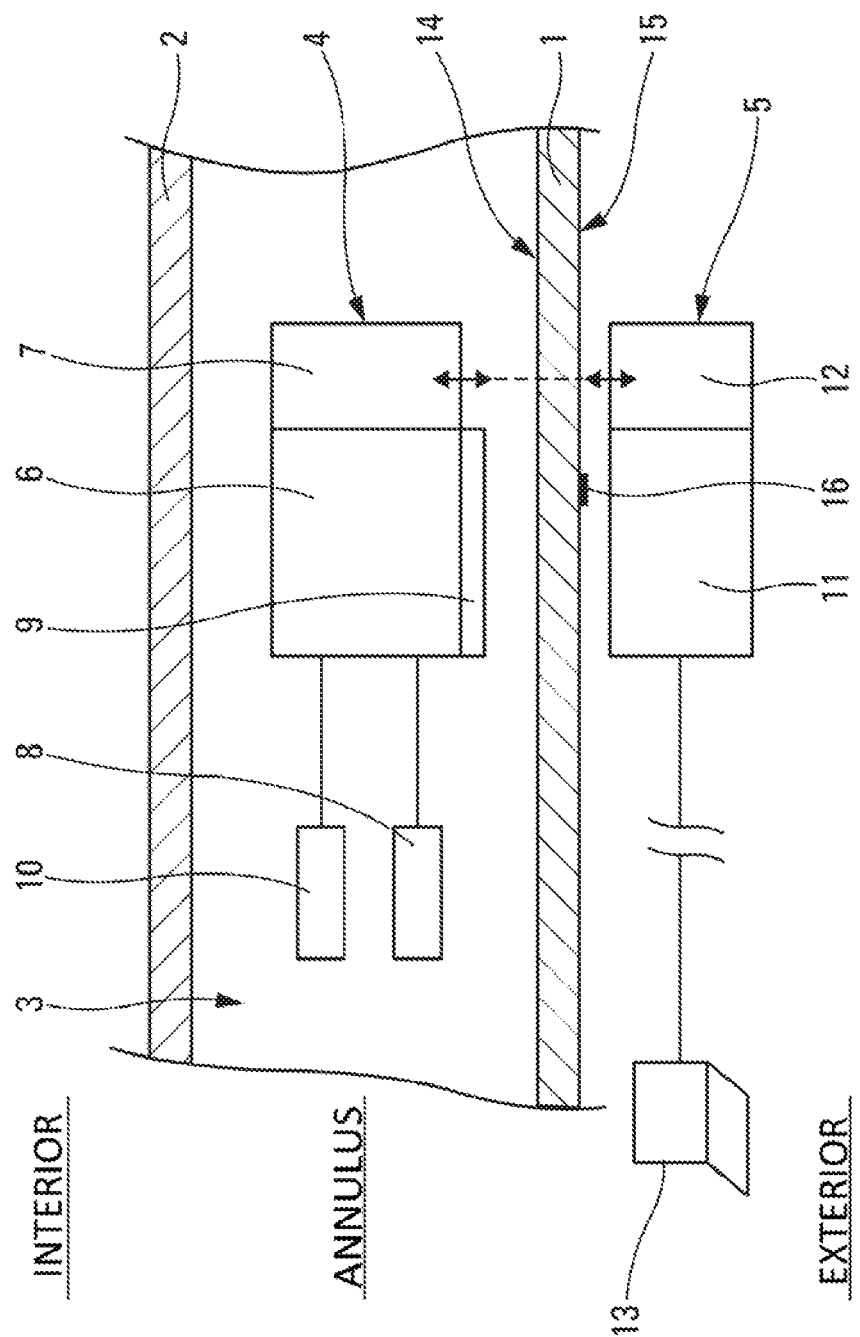
FIG. 1 shows the structure of the device according to the invention.

FIG. 1 partially shows the external pipe 1 and the inner pipe 2 of a pipe-in-pipe pipeline equipped with the device to measure a physical quantity such as pressure, hygrometry, temperature or other quantity, in the annulus 3 sealed and under reduced pressure. These pipes 1 and 2 are usually metallic.

This device is constituted by a first emitter/receiver communication assembly 4 and a second emitter/receiver communication assembly 5 each arranged facing one another on either side of the external pipe 1. The first assembly 4 is arranged in the annulus 3 against the inner wall of the external pipe 1 whereas the second assembly 5 presses against the outer wall of this external pipe as will be explained hereafter.

Advantageously, the first emitter/receiver communication assembly 4 is a first acoustic transducer fixed against the inner wall of the external pipe and the second external emitter/receiver assembly 5 is a second acoustic transducer arranged against the outer wall of the external pipe.

The first emitter/receiver assembly 4 comprises a measurement sensor 10 of the physical quantity associated with data acquisition electronics 6, a data storage memory 7, a power source, for example batteries, and an inner module 8 for wireless ultrasound communication through the steel wall of the pipe. The sensor 10 is a gauge to measure the pressure, and/or temperature, and/or hygrometry within the annulus 3. The sensor 10 is able to function in the pressure, temperature and hygrometry range that the application aims to cover.

Figure 2:
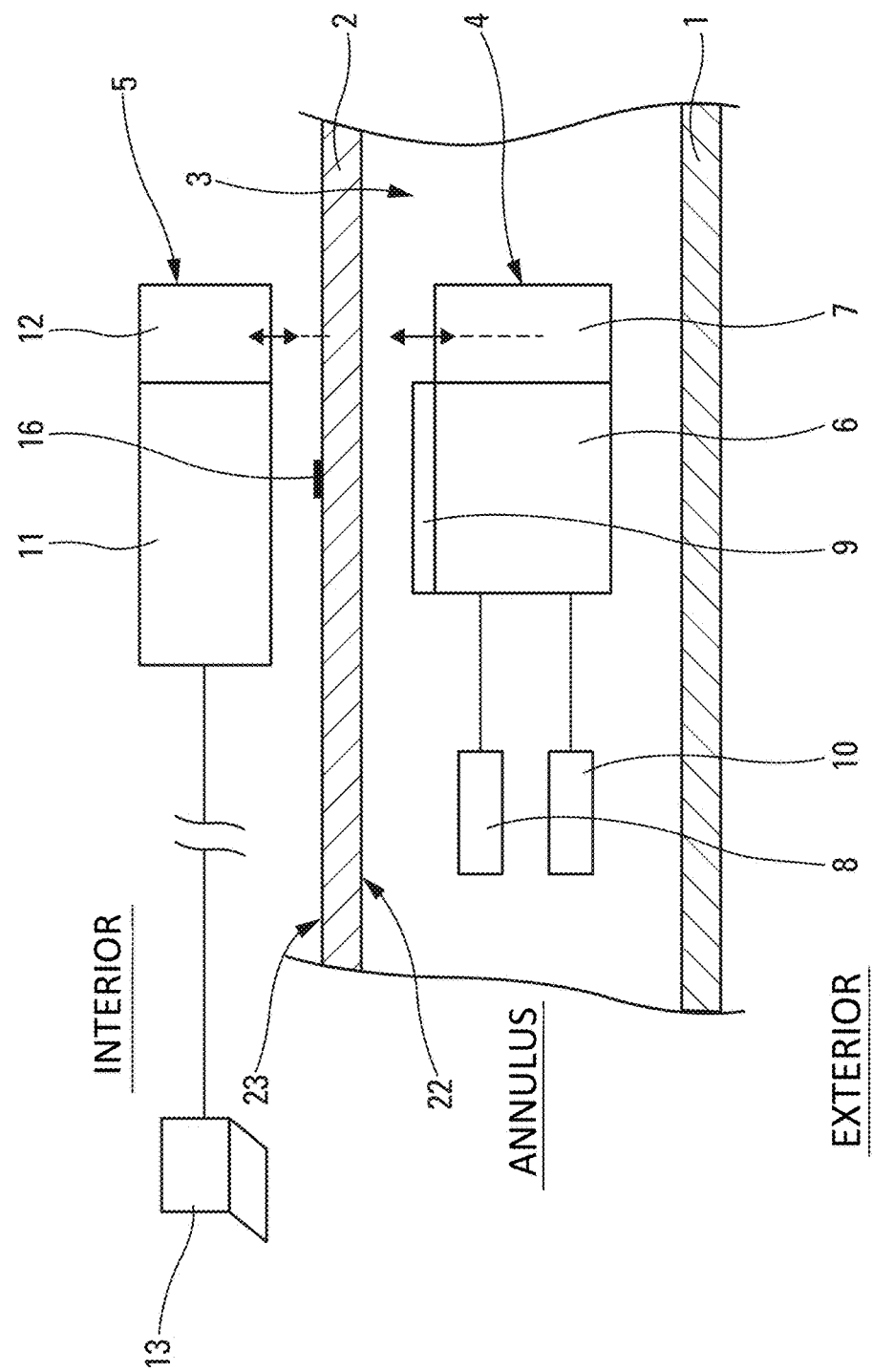
FIG. 2 shows a variant embodiment of the device according to the invention.

This first transducer assembly is naturally in the form of a compact structure that is held against the inner wall of the pipe 1, for example by a magnet not shown, or other equivalent means ensuring good mechanical contact. For this, this assembly is shaped according to the concavity of the inner wall 14 of the external pipe 1 to form a close fit as can be seen in FIG. 2. Given that the wall 14 is globally cylindrical in shape, the cowling of the assembly 4 can be performed with no real difficulty. It goes without saying that the adhesion of the assembly 4 to the inner wall 14 may be made by any means that do not damage this wall, for example using a magnet, by bonding or pressing with a spring.

It goes without saying that the assembly 4 is positioned in the annulus 3 of the pipe-in-pipe pipeline 3 when this is being manufactured and before the annulus is sealed closed. The size of this assembly 4 is determined so as to be placed in the annulus whose diameter is of around 4 to 60 mm. The communication module 8 further integrates a high frequency oscillator to communicate by ultrasound through the wall of the pipe 1, for example by means of piezoelectric ceramics.

It also goes without saying that the position of the assembly 4 is marked during the manufacture of the pipeline by easily identifiable marking means 16 on the external surface 15 of the pipe 1 or by precise reference points measured from a characteristic element of the pipe-in-pipe pipeline. Naturally, a predetermined point on the external pipe based on which the means 16 will be positioned will be easily determined.

This identification by marking or measured reference points will be made with the necessary tolerance for the selected data transmission technology. Thus, the acoustic transducers in example 1 must be positioned on either side of the metallic wall of the pipe 1, facing one another, with a tolerance of approximately 0.5 mm to 5 mm.

The second emitter/receiver assembly 5 comprises an external communication module 12 associated with a data receiver or transmitter interface. This second assembly 5 enables the measurements made of the physical quantities to be read by means of a computer, for example with a USB connection. Thus, outside the annulus 3, an operator is able to consult the sensor part 10 thanks to the emitter 8/receiver 12 system that receives the data stored in the memory 7.

In an analogous manner, the second assembly 5 is shaped to fit the outer wall 15 of the external pipe 1 following its curvature so as to position the emitter 8/receiver 12 facing one another for the measurement. This assembly 5 may naturally either be removed during measurements taken in the workshop or permanent if different measurements are required to be performed during the lifetime of the pipeline.

By way of example, the required application in the invention may cover a temperature of between 20° C. and 150° C. and a reduced pressure of $10^{-5}$ to 10,000 Pa. As for the hygrometry, it goes without saying that it must be as low as possible or even nil.

During its use, the non-intrusive measurements of the pressure, temperature or hygrometry present in the annulus 3 of a pipe-in-pipe pipeline are transmitted by ultrasound through the thickness of the external pipe 1, which does not require it to be pierced and thus causes no intrusive operations. Thus, there is no linking wire between the interior and the exterior to enable the detector in the annulus to communicate with the external reader. This has the advantage of not weakening the wall of the external pipe since pipe-in-pipe pipelines are used in environments with high hydrostatic pressures (seabed or oil wells) and the use of a perforated wall causes leaks or weakens the wall of the external pipe which thereafter has less resistance to hydrostatic pressure or to chemical loads.

The use of a transducer system according to the invention in the annulus of pipe-in-pipe pipelines enables the continuous monitoring of each physical quantity in the annulus required by the operator. Furthermore, the measurement is almost instantaneous contrary to measurements made by thermal test which require a time of 1 to 3 days to be implemented. Thus, an instantaneous measurement of pressure in the annulus enables the pressure reached to be indicated and allows it to be determined if the product satisfies the product specifications.

Lastly, the invention allows measurements to be made over a long duration during a very high temperature test, and ageing test, a test on annulus of great length of the type wound/unwound pipe-in-pipe pipelines, pipelines for the overland transportation of oils, emulsions or steam, thermally insulated pipes of the "coiled tubing" type used in oil well applications and pipelines of great length.

FIG. 2 shows a variant embodiment of the device according to the invention, the reference numbers for identical elements being retained. In this embodiment, the measurements are performed from the inside of the pipeline segment. To this end, the first internal emitter/receiver assembly 4 is a first acoustic transducer fixed to and remaining in the annulus 3. It is arranged against the outer wall of the internal pipe 2. The second external emitter/receiver assembly 5 is a second acoustic transducer arranged to the exterior of the annulus 3 and inside the internal pipe 2. It is arranged against the inner wall of the internal pipe 2. It goes without saying that the computer 13 is placed to the exterior of the internal pipe 2 so as to be able to perform the measurements as explained with reference to FIG. 1.

Figure 3:
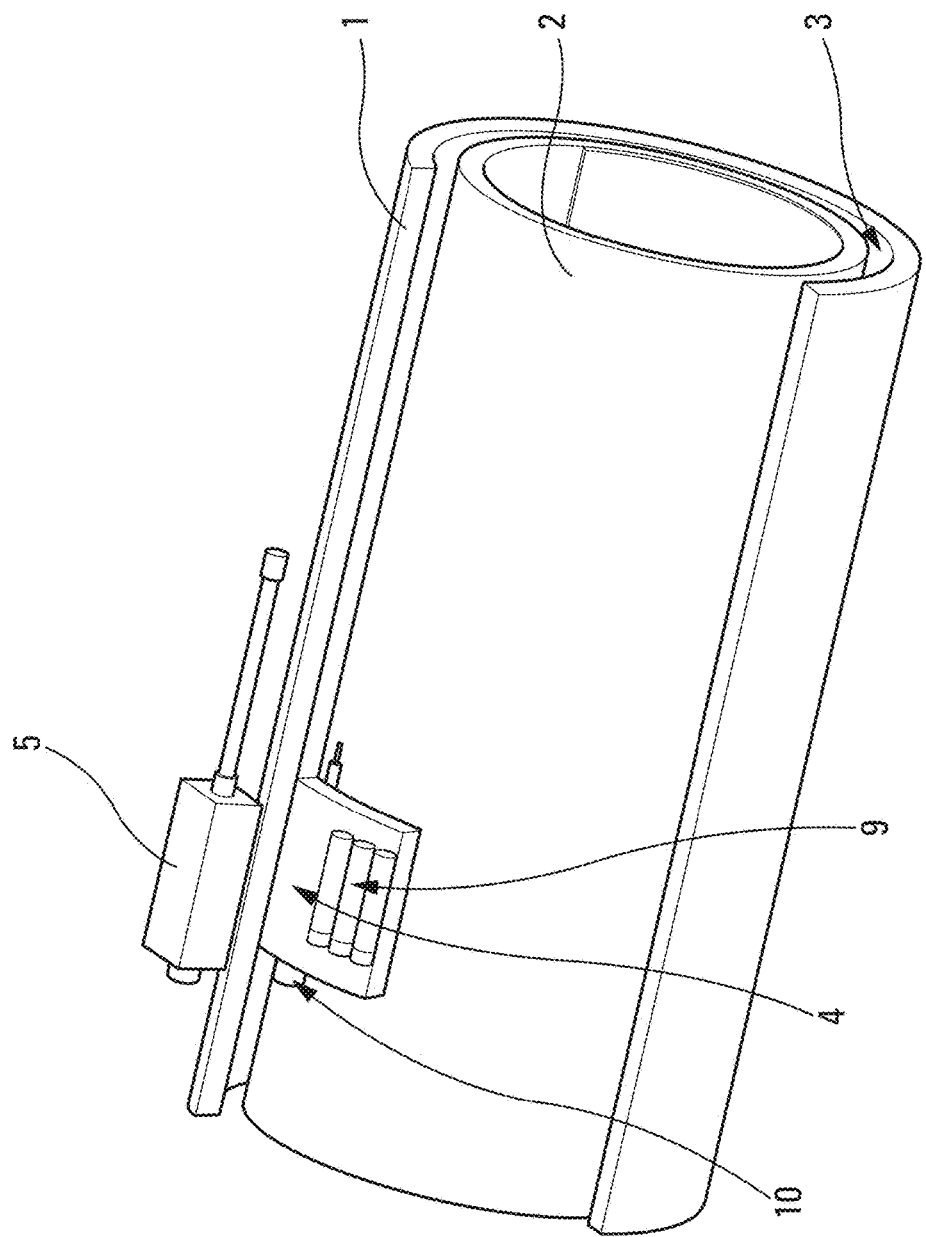
FIG. 3 shows the installation of the device in the annulus of a pipe-in-pipe pipeline.

FIG. 3 shows an example embodiment of the device according to the invention. This shows the pipe-in-pipe pipeline constituted by an inner pipe 2 inserted into an outer pipe 1 delimiting an annulus 3 between them. The assembly 4 can be seen to be made integral with the inner wall of the external pipe 1 at any point on it. As indicated previously, the position of this assembly 4 must be marked with the necessary tolerances by temporary or permanent marking means on the outer wall 15 of the pipe 1.

On the outer wall of the pipe 1, during the measurement the assembly 5 is positioned vertical to the assembly 4 thanks to the marking made on the outer wall of the external pipe or by using the reference points defined during the installation of the assembly and measured from a specific point on the pipe-in-pipe pipeline, as indicated previously. This reference point may be, for example, the extremity of this pipe-in-pipe pipeline.

It goes without saying that the assembly 5 is powered classically from outside the pipeline. The data delivered by the assembly 5 are processed, as indicated previously, by the computer 13 and enable verification of the good transmission of the signal and start of the measurement.

Figure 4:
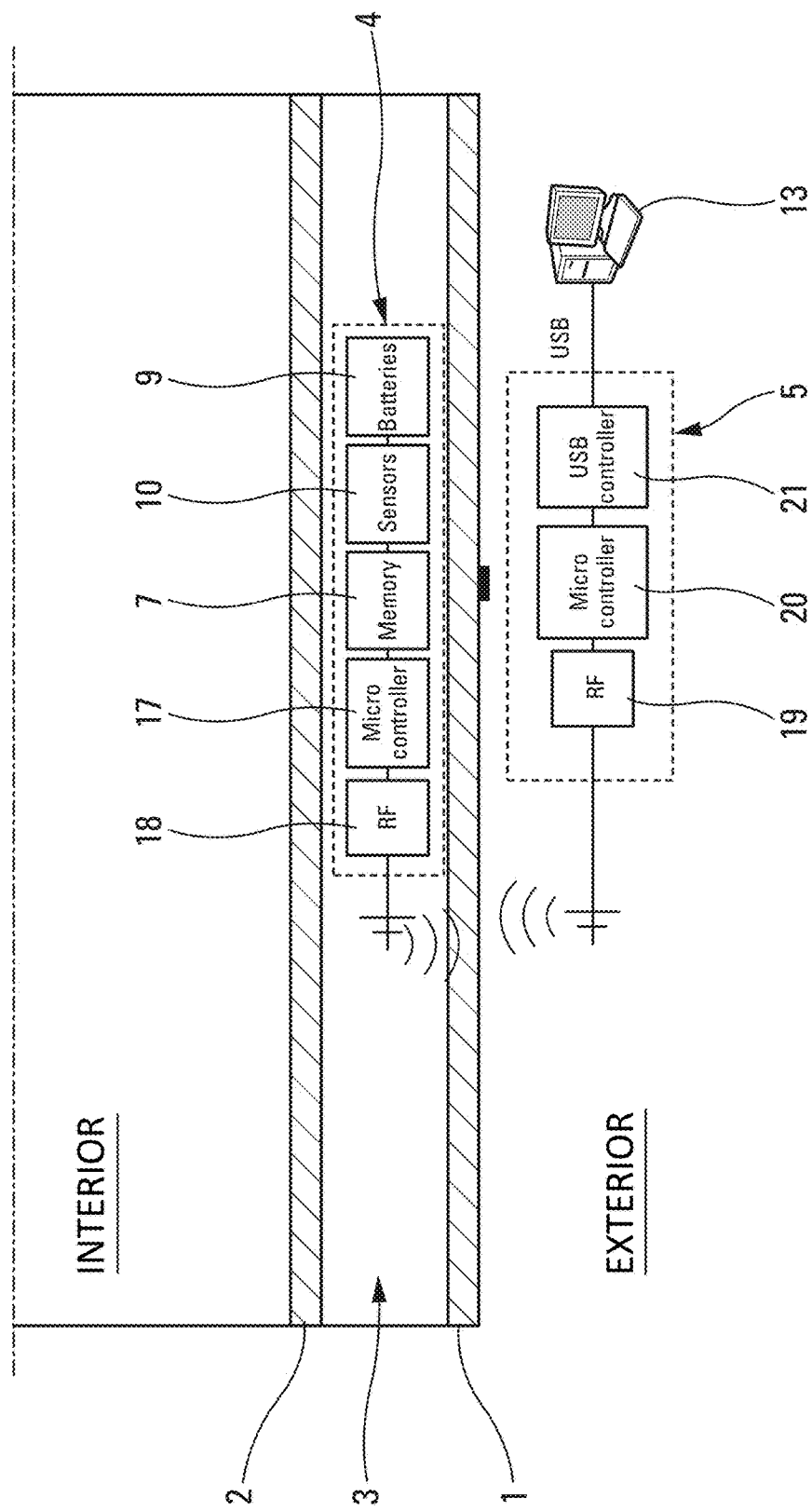
FIG. 4 shows a functional system by electromagnetic communication.

FIG. 4 shows a block diagram of the electromagnetic communication measurement system that is strictly equivalent to the one described with reference to FIGS. 1 and 2. Here again it the assembly 4 constituted by the same elements, which is to say the battery 9, the detector 10, the memory 7 and a micro-controller 17 and the electromagnetic wave generator 18. Similarly, the assembly 5 comprises a micro-controller 20, a receiver 19 for the electromagnetic waves and control means 21 for the USB connection.

What is claimed is:

1. A segment of pipe-in-pipe pipeline comprising
    a metallic internal pipe;
    a metallic external pipe, wherein an annulus under reduced pressure is sealed and delimited by the metallic internal pipe inserted into the metallic external pipe;
    a first internal emitter/receiver assembly placed inside the annulus and cooperating with a sensor to measure a first physical quantity such as pressure, hygrometry or temperature inside the reduced pressure annulus; and
    a second external emitter/receiver assembly arranged inside the internal pipe against an inner surface of the internal pipe and facing the first internal emitter/receiver assembly,
    wherein the first internal emitter/receiver assembly and the second external emitter/receiver assembly determines in a non-intrusive manner a state of the annulus.

2. A segment of pipe-in-pipe pipeline according to claim 1, further comprising identification markers arranged on an outer surface of said external pipe to locate a position of said first internal emitter/receiver assembly.

3. A segment of pipe-in-pipe pipeline according to claim 1, wherein said first internal emitter/receiver assembly is a first acoustic transducer fixed to an outer surface of said internal pipe and the second external emitter/receiver assembly is a second acoustic transducer.

4. A segment of pipe-in-pipe pipeline according to claim 3, wherein said first acoustic transducer comprises the first physical quantity measurement sensor associated with data acquisition electronics and wherein said second acoustic transducer comprises an external communication module associated with a data receiver or transmitter interface.

5. A segment of pipe-in-pipe pipeline according to claim 1, wherein said first acoustic transducer and said second acoustic transducer are formed to fit a curvature of the inner and outer surfaces of said internal pipe.

6. A segment of pipe-in-pipe pipeline according to claim 1, wherein said first internal emitter/receiver assembly and said second internal emitter/receiver assembly are formed by electromagnetic induction loops.

7. A segment of pipe-in-pipe pipeline according to claim 1, wherein said first internal emitter/receiver assembly is powered by batteries.

* * * * *